United States Patent [19]

Wilson

[11] 4,147,784

[45] Apr. 3, 1979

[54] 4,5-DIHYDRO-4-OXO-1,3-DITHIOLO(4,5-d)PYRIDAZINE-2-YLIDENE-PROPANEDINITRILES

[75] Inventor: Charles A. Wilson, Midland, Mich.

[73] Assignee: The Dow Chemical Company, Midland, Mich.

[21] Appl. No.: 889,807

[22] Filed: Mar. 24, 1978

[51] Int. Cl.² .................... C07D 495/04; A61K 31/50
[52] U.S. Cl. ...................................... 424/250; 544/235
[58] Field of Search ......................... 544/235; 424/250

[56] References Cited

U.S. PATENT DOCUMENTS

| 4,038,393 | 7/1977 | Miyan et al. | 424/250 |
| 4,075,204 | 2/1978 | Wilson et al. | 260/250 BN |
| 4,075,205 | 2/1978 | Wilson et al. | 424/250 |

OTHER PUBLICATIONS

Foye et al., J. Pharm. Sci., 57, 1611–1613 (1968).
Foye et al., J. Pharm. Sci., 64, pp. 211, 216 (1975).

*Primary Examiner*—Mark L. Berch

[57] ABSTRACT

Novel compounds corresponding to the formula

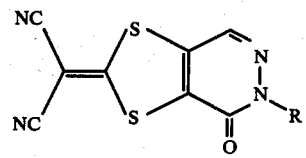

wherein R is H, an alkyl group having from 1 to about 7 carbon atoms, or

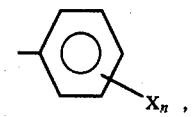

wherein X is Cl or Br and n is 0,1 or 2. Their method of use in the control and kill of bacteria and fungi, and compositions containing the compounds as active ingredients are claimed.

15 Claims, No Drawings

4,5-DIHYDRO-4-OXO-1,3-DITHIOLO(4,5-d)PYRIDAZINE-2-YLIDENE-PROPANEDINITRILES

SUMMARY OF THE INVENTION

The novel compounds of the present invention, hereinafter alternatively referred to as active compounds, correspond to the formula

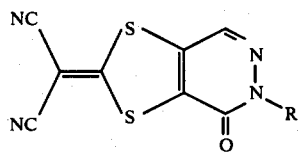

wherein R is H, an alkyl group having from 1 to about 7 carbon atoms, or

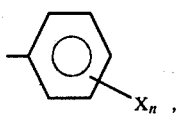

wherein X is Cl or Br and n is 0, 1 or 2. Examples of suitable alkyl groups are methyl, ethyl, n-propyl, isopropyl, n-butyl, sec-butyl, isobutyl, tert-butyl, n-pentyl and n-hexyl.

The active compounds, directly or as active ingredients in formulations and compositions, exhibit, in antimicrobially-effective amounts, antimicrobial activity against fungi and bacteria. Hereinafter the terms "antimicrobial" and "antimicrobially-effective", when used in conjunction with the active compounds, will be employed to identify their activity against fungi and/or bacteria.

The active compounds are prepared by adding a corresponding 4,5-dihalo-3-pyridiazone to disodium-dimercaptomethylene malonitrile in dimethylformamide (DMF) as exemplified by the following equation:

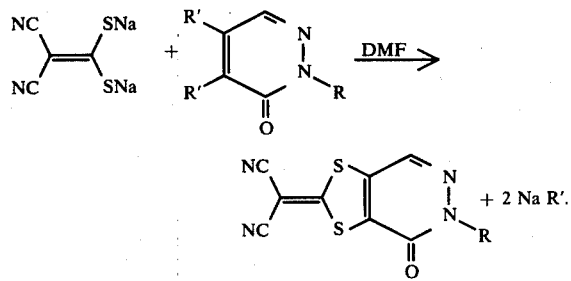

wherein R is as defined hereinbefore, and R' is a halogen selected from Br or Cl.

The reaction mixture is stirred from about 10° C. to about 50° C. until substantial completion of the reaction, usually from about 0.25 to about 1 hour. Upon completion of the reaction, the mixture is poured into water and allowed to stand for at least about 4 hours, during which time a solid product will precipitate. The solid is recovered by filtration, washed and dried. The compound can be used as prepared, however if desired it can be further purified by conventional techniques known to one skilled in the art.

Either of the starting materials can be used in excess of the stoichiometric requirements. However, ordinarily substantially equimolar proportions are employed.

The active compounds are slightly soluble in acetone and chloroform and are insoluble in water.

DESCRIPTION OF THE PREFERRED EMBODIMENTS

The following examples illustrate the present invention and the manner by which it can be practiced but as such should not be construed as limitations upon the overall scope of the same.

Example 1—Preparation of 4,5-Dihydro-4-oxo-1,3-dithiolo (4,5-d)-pyridazine-2-ylidene-propanedinitrile (Compound 1)

To a stirred solution of 20 g (0.1 mole) disodium-dimercaptomethylene malononitrile dissolved in 250 ml of DMF was added 16.5 g (0.1 mole) of 4,5-dichloro-3-pyridiazone. The reaction mixture was stirred at room temperature (approximately 20° C.) for 0.25 hours and was thereafter poured with stirring into 1 liter of water. The resulting mixture was allowed to stand for four hours during which time a yellow-gray precipitate slowly formed. This precipitate was separated by filtration, washed with water, and dried in vacuo to yield 21.1 g (90% yield from the pyridiazone) of a yellow-gray solid, m.p. (decomposition) 310°–340° C.

A sample was subjected to elemental analysis. The results obtained were as follows:

Analysis for $C_8H_2N_4OS_2$: Calcd.: C, 41.01; H, 0.86; N, 23.92. Found: C, 40.20; H, 1.09; N, 23.92.

Infra-red spectrophotometry confirmed the assigned structure.

Example 2—Preparation of 2-(4,5-Dihydro-4-oxo-5-phenyl-1,3-dithiolo(4,5-d)pyridazine-2-ylidene)-propanedinitrile (Compound 2)

To a stirred solution of 10.2 g (0.05 moles) of disodiumdimercaptomethylene malononitrile and 200 ml of DMF was added 9 g (0.05 moles) of 4,5-dichloro-2-methyl-3-(2-H)pyridiazone. The reaction mixture was stirred for 1 hour at approximately 20° C. and then poured with stirring into 1 liter of water. The resulting mixture was allowed to stand for 2 hours during which time a tan precipitate slowly formed. The precipitate was separated by filtration, washed several times with water, and dried in vacuo to yield 5.7 g (46% yield) of a tan solid, m.p. 240.1° C.

A sample was subjected to elemental analysis. The results obtained were as follows:

Analysis for $C_9H_4N_4OS_2$: Calcd.: C, 43.54; H, 1.62; N, 22.57. Found: C, 43.60; H, 1.75; N, 22.54.

Infra-red spectrophotometry confirmed the assigned structure.

The following compounds were prepared by procedures similar to those utilized in Examples 1 and 2:

Example 3—2-(4,5Dihydro-4-oxo-5-phenyl-1,3-dithiolo-(4,5-d)pyridazine-2-ylidene)-propanedinitrile (Compound 3)

The crude product, prepared from disodiumdimercaptomethylene malononitrile and 4,5-dichloro-2-phenyl-3(2H)-pyridiazone, was washed several times with distilled water and dried in vacuo to yield 11.2 g (72% yield) of a tan solid, m.p. 285°–290° C. (decomposition).

A sample was subject to elemental analysis. The results obtained were as follows:

Analysis for $C_{14}H_8N_4OS_2$: Calcd.: C, 54.18; H, 1.95; N, 18.05. Found: C, 53.90; H, 2.29; N, 17.71.

Infra-red spectrophotometry confirmed the assigned structure.

Example 4—(5-(4-Chlorophenyl)-4,5-dihydro-4-oxo-1,3-dithiolo(4,5-d)pyridazine-2-ylidene)-propanedinitrile (Compound 4)

The crude product, prepared from disodiumdimercaptomethylene malononitrile and 4,5-dichloro-2-(4-chlorophenyl)-3(2H)-pyridiazone, was washed several times with distilled water and dried in vacuo to yield 12.3 g (71% yield) of a tan solid, m.p. 295°–300° C.

A sample was subject to elemental analysis. The results obtained were as follows:

Analysis for $C_{14}H_5ClN_4OS_2$: Calcd.: C, 48.96; H, 1.46; N, 16.25. Found: C, 48.35; H, 1.71; N, 16.03.

Infra-red spectrophotometry confirmed the assigned structure.

Following the same procedures as set forth in Examples 1 thru 4 other compounds of the present invention, can readily be prepared from disodiumdimercaptomaleonitrile and the appropriate 4,5-dihalo-2-alkyl-3(2-H)pyridiazone.

The active compounds of the invention are suitable for use as antimicrobials for the control of bacteria and fungi. This is not to suggest that the active compounds and mixtures thereof with usual additives are equally effective against all such organisms at the same concentration. The active compounds can be employed in an unmodified form or dispersed on a finely divided solid and employed as a dust. Such mixtures can also be dispersed in water with the aid of a surface-active agent and the resulting emulsion employed as a spray. In other procedures, the active compounds can be employed as the active constituents in solvent solutions, oil-in-water or water-in-oil emulsions. The augmented compositions are adapted to be formulated as concentrates and subsequently diluted with additional liquid or solid adjuvants to produce the ultimate treating compositions. Good control and kill have been realized against a number of representative organisms with compositions wherein antimicrobially-effective amounts of from about 10 to about 500 parts by weight of one or more of the active compounds per million parts of such compositions are employed. As stated hereinbefore the active antimicrobially-effective amount to be employed against a given organism or in a certain composition can readily be determined by one skilled in the art.

Incorporation of the active compounds of this invention into materials which are subject to fungal attack inhibits the growth of the fungi and preserves the original value of the materials. The active compounds are sufficiently nonvolatile and water-insoluble so that they will persist on or in such materials for long periods of time. Examples of materials which are adversely affected by fungal growth are latex and alkyl paint films, wood and wooden products. The active compounds are sufficiently active against fungi such that only small quantities are required to prevent mildew on paint films or wood rot. The active compounds are therefore useful for long-term protection against fungal growth in or on materials having a wood basis or a protective or decorative paint film or other coating or covering subject to fungal attack.

In a standard activity test, samples of Compound 1 and compound 2 were individually dispersed in warm melted nutrient agar which was poured into petri dishes and allowed to solidify, the active compounds being employed in an amount sufficient to provide from 10 to 500 parts by weight thereof per million parts (ppm) of the ultimate agar composition. The surface of the agar was inoculated with a variety of bacterial and fungal pest organisms, and the inoculated plates incubated under conditions conducive to bacterial and fungal growth. Similar check plates in which the agar did not contain the active compounds or other toxic compounds were similarly inoculated and incubated.

In these studies, Compounds 1 and 2 gave 100% growth inhibition (kill) and control of the following organisms, as set forth in the Table, at the indicated concentrations in parts per million (ppm):

TABLE

| | Antimicrobial Activity | |
|---|---|---|
| | Concentration in ppm | |
| Organism | Compound 1 | Compound 2 |
| S. aureus | 50 | 10 |
| S. typhosa | 10 | 50 |
| A. niger | 500 | 50 |
| A. Fumigatus | 500 | 50 |
| C. albicans N | 500 | 50 |
| C. albicans D | 500 | 50 |
| B. subtilis | 500 | 10 |
| P. sp. strain 10 | 500 | 500 |
| C. ips | 500 | 10 |
| P. chrysogesum | 500 | 50 |

In similar studies, Compound 3 gave 100% growth inhibition (kill) and control of T. mentagrophytes at 50 ppm, and 100% kill and control of C. albicans N and D, P. Pullulans, C. ips, P. chrysogesum, A. fumigatus and A. niger at 500 ppm. Similarly, Compound 4 gave 100% kill and control of T. mentagrophytes at 50 ppm.

What is claimed is:

1. A compound of the formula

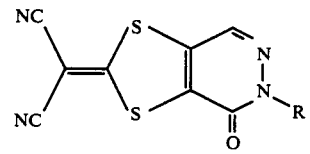

wherein R is H, an alkyl group having from 1 to 7 carbon atoms, or

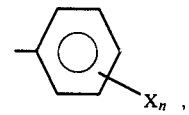

wherein X is Cl or Br and n is 0,1 or 2.

2. The compound of claim 1 wherein R is H.
3. The compound of claim 1 wherein R is methyl.
4. The compound of claim 1 wherein R is phenyl.
5. The compound of claim 1 wherein R is 4-chlorophenyl.
6. A method for controlling bacteria or fungi which comprises the step of applying to bacteria and/or fungi or their habitat an antimicrobially-effective amount of a compound of the formula.

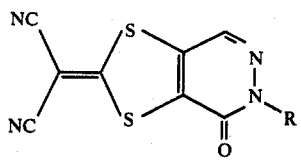

wherein R is H, an alkyl group having from 1 to 7 carbon atoms, or

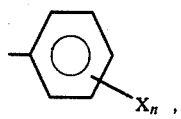

wherein X is Cl or Br and n is 0,1 or 2.

7. The method of claim 6 wherein R is H.
8. The method of claim 6 wherein R is methyl.
9. The method of claim 6 wherein R is phenyl.
10. The method of claim 6 wherein R is 4-chlorophenyl.

11. A composition for controlling bacteria or fungi comprising an antimicrobially-effective amount of a compound of the formula

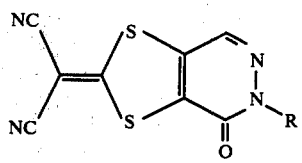

wherein R is H, or an alkyl group having from 1 to 7 carbon atoms, or

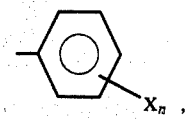

wherein X is Cl or Br and n is 0, 1 or 2, in combination with a solid or liquid diluent medium.

12. The composition of claim 11 wherein R is H.
13. The composition of claim 11 wherein R is methyl.
14. The composition of claim 11 wherein R is phenyl.
15. The composition of claim 11 wherein R is 4-chlorophenyl.

* * * * *